United States Patent [19]

Jacobson et al.

[11] Patent Number: 5,780,481

[45] Date of Patent: Jul. 14, 1998

[54] METHOD FOR INHIBITING ACTIVATION OF THE HUMAN A3 ADENOSINE RECEPTOR TO TREAT ASTHMA

[75] Inventors: Marlene A. Jacobson, Elkins Park, Pa.; Richard Norton, Somerset; Prasun K. Chakravarty, Edison, both of N.J.

[73] Assignee: Merck & Co., Inc., Rahway, N.J.

[21] Appl. No.: 694,061

[22] Filed: Aug. 8, 1996

[51] Int. Cl.$^6$ .................. A61K 31/44; A61K 31/41; A61K 31/34

[52] U.S. Cl. .................. 514/293; 514/294; 514/359; 514/461

[58] Field of Search .................. 514/293, 294, 514/359, 461

[56] References Cited

FOREIGN PATENT DOCUMENTS

| 2 264 948 | 9/1993 | United Kingdom. |
| 95/11681 | 5/1995 | WIPO. |

OTHER PUBLICATIONS

Salvatore et al., Proc. Natl. Acad. Sci. USA, "Molecular cloning and characterization of the human A3 adenosine receptor", vol. 90, pp. 10365–10369 (1993).

Katritzky et al., Croatica Chemica Acta, "Cycloaddition Reaction Involving Two Heterocyclic Rings. Preparation of Novel Triazolonaphthyridine Ring Systems", vol 59 (1), pp. 27–32 (1986).

Primary Examiner—Theodore J. Criares
Attorney, Agent, or Firm—Richard S. Parr; Melvin Winokur

[57] ABSTRACT

The invention is a method for inhibiting activation of the human A3 adenosine receptor with adenosine, by treating the receptor a compound of the formula

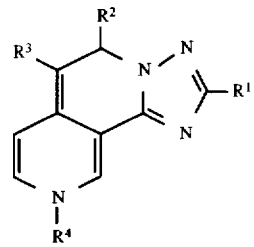

e.g., 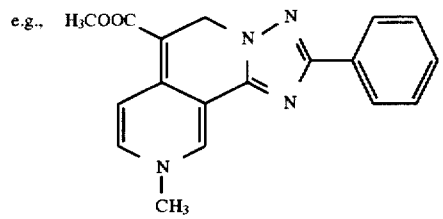

to treat asthma.

5 Claims, 1 Drawing Sheet

METHOD FOR INHIBITING ACTIVATION OF THE HUMAN A3 ADENOSINE RECEPTOR TO TREAT ASTHMA

BACKGROUND OF THE INVENTION

The present invention concerns the use of compounds as antagonists of the A3 adenosine receptor subtype for preventing mast cell degranulation and are therefore useful in the treatment or prevention of disease states induced by activation of the A3 receptor and mast cell activation. These disease states include but are not limited to asthma, myocardial reperfusion injury, allergic reactions including but not limited to rhinitis, poison ivy induced responses, urticaria, scleroderma, arthritis, other autoimmune diseases and inflammatory bowel diseases.

The actions of adenosine are mediated through G-protein coupled receptors, the A1, A2a, A2b and A3 adenosine receptors. The adenosine receptors were initially classified into A1 and A2 subtypes on the basis of pharmacological criteria and coupling to adenylate cyclase (Van Caulker, D., Muller, M. and Hamprecht, B. (1979) *J. Neurochem.*, 33:999–1003). Further pharmacological classification of adenosine receptors prompted subdivision of the A2 class into A2a and A2b subtypes on the basis of high and low affinity, respectively, for adenosine and the agonists NECA and CGS-21680 (Bruns, R. F., Lu, G. H. and Pugsley, T. A. (1986) *Mol. Pharmacol.*, 29:331–346; Wan, W., Sutherland, G. R. and Geiger, J. D. (1990) *J. Neurochem.*, 55:1763–1771). Molecular cloning and characterization of the human A3 adenosine receptor is described in Salvatore et al., *Proc. Natl. Acad. Sci. U.S.A.*, vol. (90) pp 10365–10369, November 1993. The existence of A1, A2a, A2b and A3 subtypes has been confirmed by cloning and functional characterization of expressed bovine, canine, rat and human receptors. Cloning and characterization of the human A1, A2a, A2b and A3 receptors are described in GB 2264948-A. Based on the use of these cloned receptors, an assay has been described to identify adenosine receptor agonists and antagonists and determine their binding affinity (see GB 2 264 948 A, published Sep. 15, 1993; see also R. F. Bruns, et al., (1983) *Proc. Natl. Acad. Sci. U.S.A.*, 80:2077–2080; R. F. Bruns, et al.,(1986) *Mol. Pharmacol.*, 29:331–346; M. F. Jarvis, et al. (1989) *J. Pharma. Exp. Therap.*, 251:888–893; K. A. Jacobson et al., (1989) *J. Med. Chem.*, 32:1043–1051).

Adenosine exhibits diverse and potent physiological actions in the cardiovascular, nervous, pulmonary, renal and immune systems. Adenosine has been demonstrated to terminate superventricular tachycardia through blockage of atrioventricular nodal conduction (J. P. DiMarco, et al., (1985) *J. Am. Col. Cardiol.*, 6:417–425, A. Munoz, et al., (1984) *Eur. Heart J.*, 5:735–738). Adenosine is a potent vasodilator except in the kidney and placenta (R. A. Olsson, (1981) *Ann. Rev. Physiol.*, 43:385–395). Adenosine produces bronchoconstriction in asthmatics but not in nonasthmatics (Cushly et al., 1984, *Am. Rev. Respir. Dis.*, 129:380–384). Adenosine has been implicated as a preventative agent and in treatment of ventricular dysfunction following episodes of regional or global ischemia (M. B. Forman and C. E. Velasco (1991) *Cardiovasc. Drugs and Therapy*, 5:901–908) and in cerebral ischemia (M. C. Evans, et al., (1987) *Neurosci. Lett.*, 83:287, D. K. J. E., Von Lubitz, et al., (1988) *Stroke*, 19:1133).

Adenosine receptor agonists, antagonists and binding enhancers have been identified and implicated for usage in the treatment of physiological complications resulting from cardiovascular, pulmonary, renal and neurological disorders. Adenosine receptor agonists have been identified for use as vasodilators ((1989) *FASEB. J.*, 3(4) Abs 4770 and 4773, (19910 *J. Med. Chem.*, (1988) 34:2570), antihypertensive agents (D. G. Taylor et al., *FASEB J.*, (1988) 2:1799), and anti-psychotic agents (T. G. Heffner et al., (1989) *Psychopharmacology*, 98:31–38). Adenosine receptor agonists have been identified for use in improving renal function (R. D. Murray and P. C. Churchill,(1985) *J. Pharmacol. Exp. Therap.*, 232:189–193). Adenosine receptor allosteric or binding enhancers have shown utility in the treatment of ischemia, seizures or hypoxia of the brain (R. F. Bruns, et al. (1990) *Mol. Pharmacol.*, 38:939–949; C. A. Janusz, et al., (1991) *Brain Research*, 567:181–187).

Methods of treating conditions related to the physiological action of adenosine have, to date, proven inferior due to the nonselectivity of the compounds for the multiple adenosine receptor subtypes present in whole tissue. (R. F. Bruns et al., (1986) *Mol. Pharm.*, 29:331–346) and the inability to extrapolate activities measured on non-human tissues due to the species variability in the affinity for adenosine analogs and the physiological effects of adenosine (Ukera, et al., (1986) *FEBS Lett*, 209:122–128, Stone, et al.(1988) 15, 31–46).

We have identified compounds which selectively inhibit the human adenosine A3 receptor subtype and therefore provide a method of using such compounds which overcomes the disadvantages of using compounds of uncharacterized specificity.

SUMMARY OF THE INVENTION

The invention concerns the use of compounds to modulate the physiologic role of adenosine activation of the A3 receptor.

The invention is a method for inhibiting activation of the human A3 adenosine receptor with adenosine, by treating the receptor with a compound of the formula

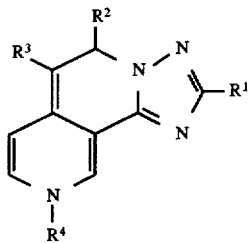

and pharmaceutically acceptable salts, wherein
$R^1$ is
  (a) phenyl or pyrimidyl optionally substituted with one or two substituents selected from the group consisting essentially of $C_1$–$C_4$ -alkyl, bromo, chloro, fluoro, $CF_3$, $C_1$–$C_4$-alkoxy and phenyl, or
  (b) furyl, thiophenyl or thiazolyl optionally susbtituted with $C_1$–$C_4$ -alkyl or phenyl;
$R^2$ is
  hydrogen, $C_1$–$C_4$ -alkyl or phenyl;
$R^3$ is
  —CN, —COOC$_{1-4}$ alkyl, —CONH$_2$, —COOH, —CONHSO$_2$R$^5$ or 5-tetrazolyl;
$R^4$ is
  —C$_{1-4}$-alkyl optionally substituted with —COOC$_{1-4}$ alkyl, —CONH$_2$, COOH or phenyl optionally substituted with one or two substituents selected from the group consisting essentially of $C_1$–$C_4$-alkyl, bromo, chloro, fluoro, $CF_3$; $C_1$–$C_4$-alkoxy and phenyl;

$R^5$ is

—$C_1$–$C_4$ -alkyl or phenyl optionally substituted with one or two substituents selected from the group consisting essentially of $C_1$–$C_4$ -alkyl, bromo, chloro, fluoro, $CF_3$, $C_1$–$C_4$-alkoxy and phenyl, referred to hereinafter as A3 adenosine receptor antagonists.

The invention includes a method for achieving blockade of the vasoconstrictive response induced through adenosine activation of the A3 adenosine receptor subtype, which comprises treating the patient with an A3 adenosine receptor antagonist described above.

The invention also includes a method for treating or preventing myocardial ischemia, inflammation, brain arteriole diameter constriction, and the release of allergic mediators, which comprises treating the patient with an A3 adenosine receptor antagonist described above.

The invention also includes a method for treating or preventing asthma, myocardial reperfusion injury, rhinitis, poison ivy induced responses, urticaria, scleroderma, arthritis, and inflammatory bowel diseases which comprises treating the patient with an A3 adenosine receptor antagonist described abovee.

The invention also includes a method for preventing mast cell degranulation in a human which comprises treating the patient with an A3 adenosine receptor antagonist described above.

DETAILED DESCRIPTION OF THE DRAWING

Figure 1:
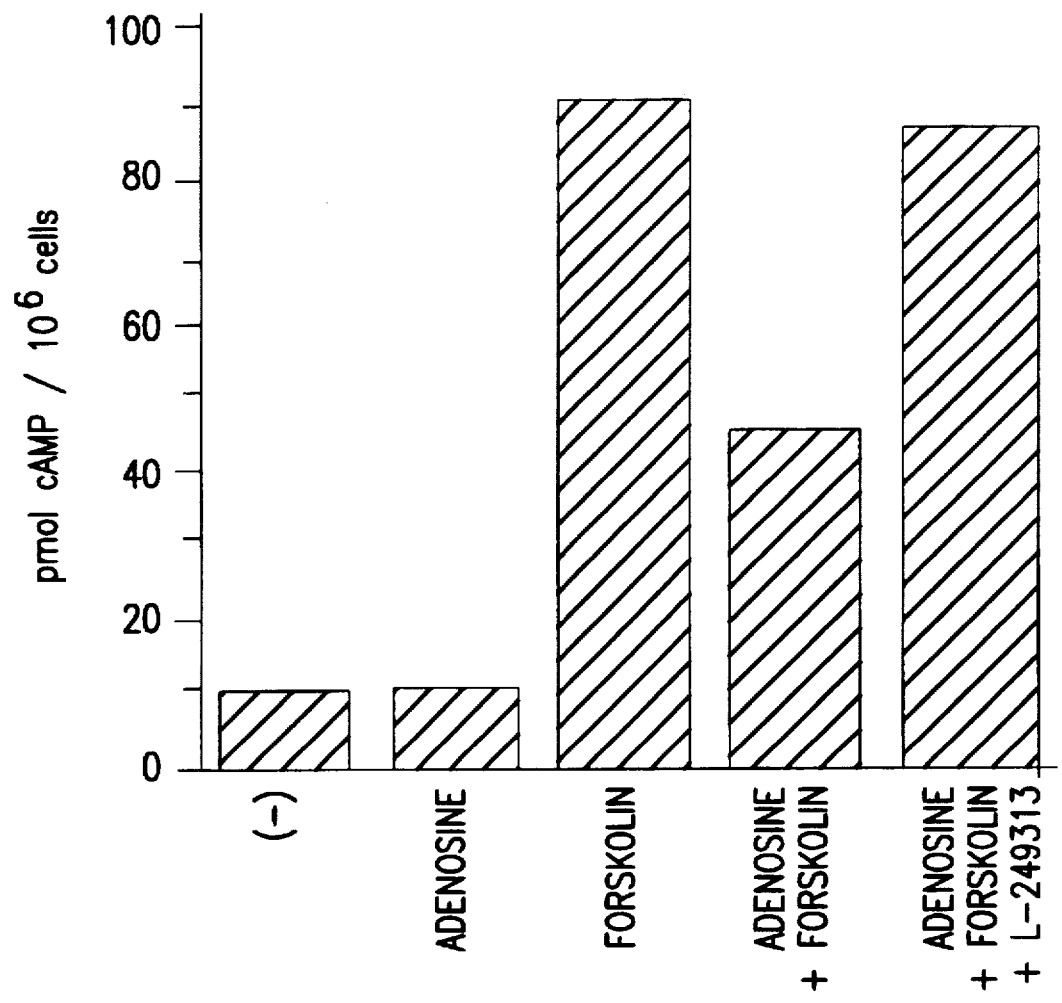

FIG. 1 shows the effect of adenosine on forskolin induced cAMP accumulation as measured in the absence and presence of 10 µM compound IV (identified below).

DETAILED DESCRIPTION OF THE INVENTION

Adenosine, adenosine metabolites and other A3 adenosine receptor agonists induce mast cell degranulation. Mast cell activation promotes the release of enzymes, bioactive amines and arachidonic acid metabolites which causes vasoconstriction, edema, leukocyte accumulation, and ultimately, tissue damage. Mast cell degranulation is associated with myocardial reperfusion injury, hypersensitivity reactions such as asthma, allergic rhinitis, urticaria, ischemic bowel disease, autoimmune diseases including autoimmune inflammation, and atopic dermatitis.

The invention consists of administering an inhibitory effective amount of the A3 adenosine receptor antagonists to treat or prevent these diseases and pathologic effects that result from mast cell degranulation. The types of diseases amenable to treatment by the method of this invention include, but are not limited to, Addison's disease, autoimmune hemolytic anemia, Crohn's disease, Goodpasture's syndrome, Grave's disease, Hashimoto's thyroiditis, idiopathic thrombocytopinic purpura, Insulin-dependent diabetes militus, multiple sclerosis, myasthenia gravis, Pemphigus vulgaris, pernicious anemia, poststreptococcal glomerulonephritis, psoriasis, rheumatoid arthritis, scleroderma, Sjogren's syndrome, spontaneous infertility, and systemic lupus erythematosus.

In one embodiment of the invention, the method provides a means for preventing or treating disease states associated with vascular constriction induced through activation of the A3 subtype of the adenosine receptor. The method comprises contacting said receptor in the vasculature with an amount of A3 adenosine receptor antagonist which selectively blocks activation of the A3 adenosine receptor subtype on granulocytes, including mast cells, exhibiting the A3 adenosine receptor. A3 adenosine receptor antagonists are used to effect a reduction in vasoconstriction in the vasculature without any substantial effect (binding or blockade) of the A1, A2a or A2b subtypes of the adenosine receptor.

The invention is a method for inhibiting activation of the human A3 adenosine receptor with adenosine, by treating the receptor with a compound of the formula

I and pharmaceutically acceptable salts, wherein $R^1$ is (a) phenyl or pyrimidyl optionally substituted with one or two substituents selected from the group consisting essentially of $C_1$–$C_4$ -alkyl, bromo, chloro, fluoro, $CF_3$, $C_1$–$C_4$-alkoxy and phenyl, or (b) furyl, thiophenyl or thiazolyl optionally susbtituted with $C_1$–$C_4$ -alkyl or phenyl;

$R^2$ is hydrogen, $C_1$–$C_4$ -alkyl or phenyl;

$R^3$ is

—CN, —$COOC_{1-4}$ alkyl, —$CONH_2$, —COOH, —$CONHSO_2R^5$ or 5-tetrazolyl;

$R^4$ is

—$C_{1-4}$-alkyl optionally substituted with —$COOC_{1-4}$ alkyl, —$CONH_2$, COOH or phenyl optionally substituted with one or two substituents selected from the group consisting essentially of $C_1$–$C_4$ -alkyl, bromo, chloro, fluoro, $CF_3$, $C_1$–$C_4$-alkoxy and phenyl; and $R^5$ is —$C_1$–$C_4$ -alkyl or phenyl optionally substituted with one or two substituents selected from the group consisting essentially of $C_1$–$C_4$ -alkyl, bromo, chloro, fluoro, $CF_3$, $C_1$–$C_4$-alkoxy and phenyl, referred to hereinafter as A3 adenosine receptor antagonists.

In one class of the invention, the compound has the formula

II and pharmaceutically acceptable salts, wherein $R^1$ is phenyl optionally substituted with one or two substituents selected from the group consisting of $C_1$–$C_4$ -alkyl, bromo, chloro, fluoro, $CF_3$, $C_1$–$C_4$-alkoxy and phenyl, or $R^2$ is hydrogen, $C_1$–$C_4$ -alkyl or phenyl;

$R^3$ is

—CN, —$COOC_{1-4}$ alkyl, —$CONH_2$, —COOH, —$CONHSO_2R^5$ or 5-tetrazolyl;

$R^4$ is

—$C_{1-4}$-alkyl optionally substituted with —$COOC_{1-4}$ alkyl, —$CONH_2$, COOH or phenyl, optionally substituted with one or two substituents selected from the group consisting of $C_1$–$C_4$-alkyl, bromo, chloro, fluoro, $CF_3$, $C_1$–$C_4$-alkoxy and phenyl; and $R^5$ is $C_1$–$C_4$-alkyl or phenyl optionally substituted with one or two substituents selected from the group consisting of $C_1$–$C_4$-alkyl, bromo, chloro, fluoro, $CF_3$, $C_1$–$C_4$-alkoxy and phenyl.

In a subclass of this class, the compound has the formula

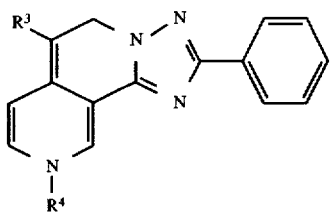

III and pharmaceutically acceptable salts, wherein $R^1$ is phenyl optionally substituted with one or two substituents selected from the group consisting of $C_1$–$C_4$-alkyl, bromo, chloro, fluoro, $CF_3$, $C_1$–$C_4$-alkoxy and phenyl, or $R^2$ is hydrogen, $C_1$–$C_4$-alkyl or phenyl;

$R^3$ is

—$COOCH_3$ or —$COOCH_2CH_3$;

$R^4$ is

—$CH_3$, —$CH_2CH_3$, —$CH_2COOCH_3$, —$CH_2COOC(CH_3)_3$, —$CH_2COOH$, -benzyl, 4-bromobenzyl or 4-chlorobenzyl; and $R^5$ is $C_1$–$C_4$-alkyl or phenyl optionally substituted with one or two substituents selected from the group consisting of $C_1$–$C_4$-alkyl, bromo, chloro, fluoro, $CF_3$, $C_1$–$C_4$-alkoxy and phenyl.

In one exemplification, the compound is

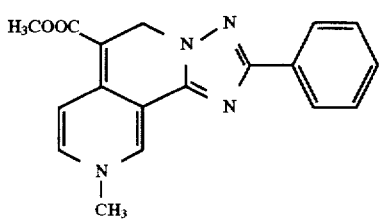

IV

In another exemplification, the compound is the methanesulfonic acid salt of the above.

The invention also includes compounds having the formula

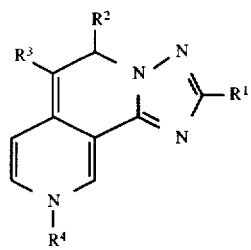

I and pharmaceutically acceptable salts, wherein $R^1$ is (a) phenyl or pyrimidyl optionally substituted with one or two substituents selected from the group consisting essentially of $C_1$–$C_4$-alkyl, bromo, chloro, fluoro, $CF_3$, $C_1$–$C_4$-alkoxy and phenyl, or (b) furyl, thiophenyl or thiazolyl optionally susbtituted with $C_1$–$C_4$-alkyl or phenyl;

$R^2$ is hydrogen, $C_1$–$C_4$-alkyl or phenyl;

$R^3$ is

—CN, —$COOC_{1-4}$ alkyl, —$CONH_2$, —COOH, —$CONHSO_2R^5$ or 5-tetrazolyl;

$R^4$ is

—$C_{1-4}$-alkyl optionally substituted with —$COOC_{1-4}$ alkyl, —$CONH_2$, COOH or phenyl optionally substituted with one or two substituents selected from the group consisting essentially of $C_1$–$C_4$-alkyl, bromo, chloro, fluoro, $CF_3$, $C_1$–$C_4$-alkoxy and phenyl; and $R^5$ is —$C_1$–$C_4$-alkyl or phenyl optionally substituted with one or two substituents selected from the group consisting essentially of $C_1$–$C_4$-alkyl, bromo, chloro, fluoro, $CF_3$, $C_1$–$C_4$-alkoxy and phenyl, provided the compound is not

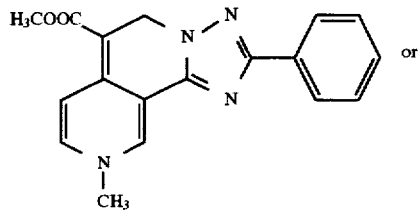

or

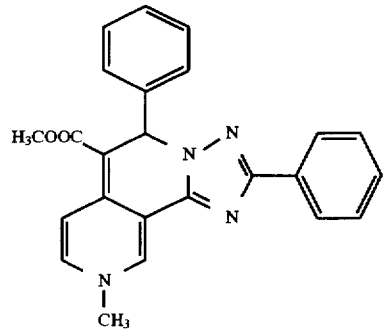

The compounds of formula I disclosed in this invention can be prepared using the general synthetic route outlined below. The key intermediate 3 can be prepared readily from the reaction of appropriately susbstituted benzoic hydrazide (2) and 3-cyanopyridine. The 3,5-diaryl-1,2,4-triazoles (intermediate 3) can be reacted with an appropriate alkyl iodide or benzyl bromide to provide the pyridinium salt 4 which then can be subjected to cycloaddition reaction with an appropriately substituted acrylate to provide the desired triazolonaphthyridine 5.

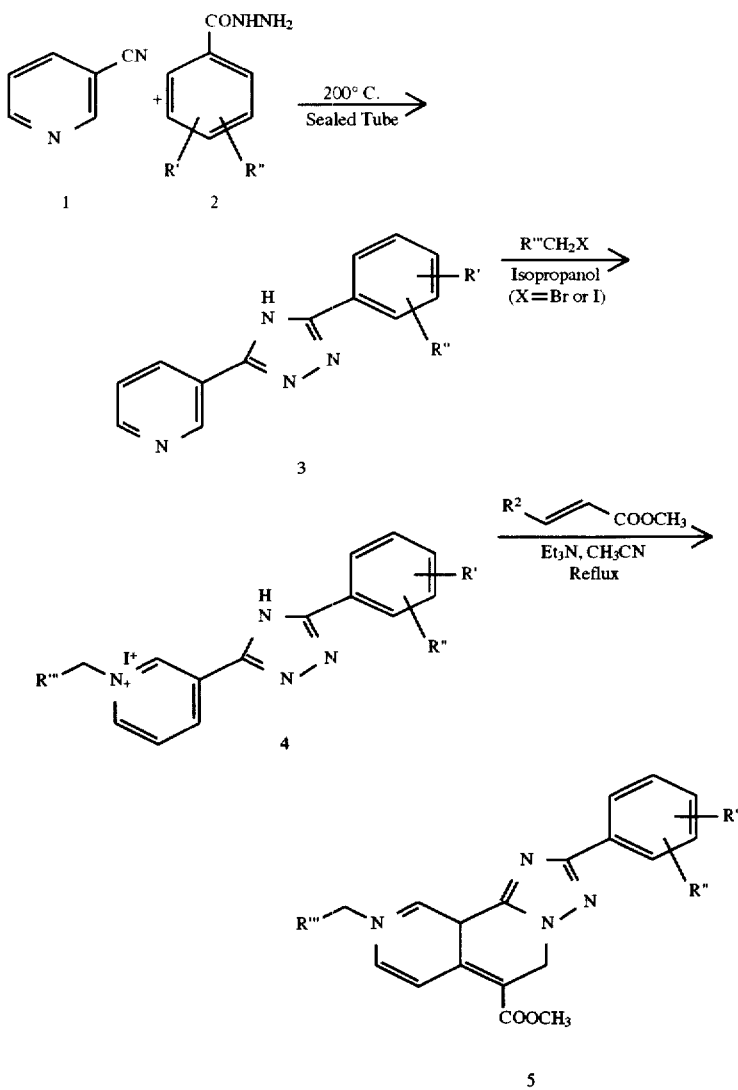

The 1,2,4-triazole intermediate can also be prepared using the variety of methods described in the literature [(1). J. B. Polya in "Comprehensive Heterocyclic Chemistry: The Structure, Reaction, Synthesis and uses of Hetreocyclic Compounds" Eds.A. R. Katritzky and C. W. Rees, Vol 5 (Ed. K. T. Potts) Pergamon press, Oxford, 1984, pp.733–790; (2) A. R. Katritzky et. al. Croat. Chem. Acta., 59, 27–32 (1986); (3) R. Kraft et al. Chem. Ber., 101, 2028–2032 (1968); (4) T. Kauffman et al. Chem. Ber, 114, 3684 (1981)].

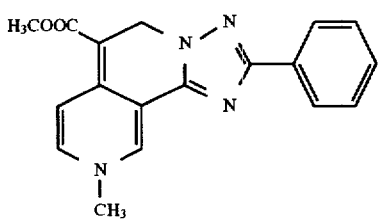

IV

Step 1: 3-phenyl-5-(pyrid-3-yl)-1,2,4-triazole

A mixture of 3-cyanopyridine (82 g, 0.788 Mol) and benzoic hydrazide (35 g, 0.257 Mol) was stirred at 200° C. for 48 h. The reaction mixture was cooled to room temperature, and the resulting solid mass was triturated with ether and filtered. The solid was washed with ether and then dried overnight under vaccum. mp. 212°–214° C. [lit.(2), mp. 211°–214° C.].

Step 2: 1-methyl-3-(3-phenyl-1,2,4-triazol-5-yl)pyridinium iodide

The product of step 1 (46 g) was dissolved in warm (60° C.) isopropanol (1000 mL). The mixture was then cooled to room temperature and methyliodide (20 mL) was added. The resulting mixture was then stirred at 50° C. for 24 h. The reaction was cooled to room temperature and filtered. The yellow crystalline solid was washed with cold isopropanol (25 mL) and the with ether. The solid was finally dried in vacuo for 12 h. mp. 237°–238° C. [lit.(2), mp. 236° C.].

Step 3: 6-carbomethoxy-2-phenyl-[1,2,4]-triazolonaphthyridine (IV)

To a suspension of the compound from step 2 (64 g) in $CH_3CN$ (1000 mL) was added methylacrylate (20 mL), and the mixure was refluxed for 45 minutes. To this mixture was then added triethylamine (75 mL) under strring. The mixture was refluxed for an additional 24 h and then cooled to room temperature. The solid product was filtered, washed with cold $CH_3CN$ (50 mL) and dried in vacuo overnight. The crude product (20.4 g), thus obtained, was stirred with 2N HCl (200 mL) and filtered. The filtrate was neutralized with $NaHCO_3$ (pH~8.0) and filtered. The solid was washed with water and dried under high vacuum ovemightto give the titled compound IV. Yield. 12.3 g. mp. 255°–258° C. [lit.(2), mp. 250° C.].

$^1$H-NMR(DMSO-$d_6$): δ3.55 (3H, s, $COOCH_3$), 3.61 (3H, s, $CH_3$), 5.15 (2H, s, $CH_2$), 7.18 (d, 1H), 7.45 (m, 3H, aromatic), 7.78 (d, 1H), 7.92 (s, 1H), 8.01 (d, 2, aromatic).

Step 4: Preparation of methansulfonic acid salt of compound IV

Compound IV (8.1 g) was dissolved in a mixture of methanol (150 mL) and ethylacetate (150 mL), and to the solution was added methanesulfonic acid (1.65 mL) under stirring at 0° C. (the color of the solution changed from yellow to light orange). After 10 mins of stirring, the solution was filtered to remove any suspended material, and the filtrate was concentrated to a small volume (10 ml) and ethylacetate (50 mL) was added. The orange precepitate (the product) was filtered and dried overnight in vacuo.

The term "alkyl" means straight or branched alkane containing 1 to about 4 carbon atoms, e.g., methyl, ethyl, n-propyl, isopropyl, n-butyl, isobutyl, sec-butyl, and tert-butyl.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

A3 adenosine receptor antagonists useful for the present invention can be prepared according to the general procedure exemplified in Katritzky et al., Croatica Chemica Acta 59 (1) pp. 27–32 (1986) for preparing triazolonaphthyridines. According to Katritzky et al., 3-cyanopyridine is reacted with benzoic hydrazide to yield 3-phenyl-5-(3-pyridyl)-1,2,4-triazole, which is then reacted with methyl iodide to give a pyridinium salt in equilibrium with betaine. Subsequent reactions with, for example, acrylonitrile, methyl acrylate, or ethyl phenylpropiolate, gave finished products.

The A3 adenosine receptor antagonists useful for the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the A3 adenosine receptor antagonist required to prevent, counter, or arrest the progress of the condition.

Oral dosages of the A3 adenosine receptor antagonists, when used for the indicated effects, will range between about 1 μg per kg of body weight (μg/kg) to about 10 mg/kg intravenously, e.g. 10 μg/kg, 1 mg/kg, or 5 mg/kg . For a typical patient, doses range from between 0.1 mg to 1 gram, e.g. 1 mg, 100 mg and 500 mg. Advantageously, A3 adenosine receptor antagonists useful for the present invention may be administered in divided doses of two, three, or four times daily.

Intravenously, the most preferred doses of A3 adenosine receptor antagonist will range from about 0.05 to about 0.25 μg/kg/minute during a constant rate infusion, e.g. 0.15 μg/kg/minute. In order to administer that amount of active ingredient, a composition of the invention having 0.05 mg/ml of active ingredient should be administered at a rate of between about 0.001 and 0.005 ml/kg/min, e.g. 0.003 ml/kg/min. Compositions of the invention containing higher concentrations of active ingredients should be administered at correspondingly lower rates.

Furthermore, preferred A3 adenosine receptor antagonists useful for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather that intermittent throughout the dosage regime.

In the methods of the present invention, the A3 adenosine receptor antagonists herein described form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices.

For instance, for oral administration in the form of a tablet or capsule, the A3 adenosine receptor antagonist component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, com-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The A3 adenosine receptor antagonists useful for the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

A3 adenosine receptor antagonists useful for the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Adenosine has been shown to produce bronchoconstriction in asthmatics but not in nonasthmatics, demonstrating that adenosine plays a role in the etiology of this disease state (Cushly et al., *AM. Rev. Respir. Dis.*, (129) pp. 380–384 (1984)). Adenosine mediated bronchoconstriction on bronchial rings in asthmatics is blocked in vitro by a combination of histamine and leukotriene antagonists (Bjorck et al., *Am. Rev. Resp. Dis.*, 1992, (145) pp. 1087–1091 (1992)), indicating that adenosine acts by releasing histamine, leukotriene and other agents from mast cells or other cells that contain these allergic mediators. A3 adenosine receptor antagonists identified herein as being useful to antagonize the A3 adenosine receptor can be used in conjunction with other therapies, including co-administration of antihistamine, leukotriene blockade or other anti-allergic mediator therapies and A3 specific antagonists.

Blockade of A3 adenosine receptor mediated action in the vasculature is useful to treat and prevent disease states in humans. Adenosine potentiates the release of granule contents from mast cells isolated from rat peritoneum (see Lohse et al., *N.-S. Arch. Pharmacol.*, (335) pp. 555–560 (1987) and Marquardt et al., *J. Immunol.*, (120) pp. 871–878 (1978)), which causes constriction in some vascular beds resulting in C5a-induced myocardial ischemia (see Ito et al., *Am. J. Physiol.*, (264) (*Heart Circ. Physiol.*, (33) pp. H1346–H1354 (1993)), mast cell-dependent inflammation (see Raud, J., *Acta. Physiol. Scand.*, (135) (Suppl., 578) pp. 1–58 (1989)), brain arteriole diameter constriction (see Rosenblum, W. I., *Brain Res.*, (49) pp. 75–82 (1973)), and the release of allergic mediators (see Ramkumar, et al., *J. Biol. Chem.*, (268) pp. 16887–16890 (1993)). These disease states can be prevented or treated by contacting A3 receptor bearing mast cells with an amount of an A3 adenosine receptor antagonist identified herein effective to prevent mast cell degranulation.

The trigger for mast cell degranulation is usually thought to be an allergen. Allergens are endocytosed by marcrophages and degraded. The resulting fragments are displayed on T lymphocytes. B lymphocytes are stimulated to mature into plasma cells which are able to secrete allergen-specific molecules known as immunoglobulin E. These antibodies attach to receptors on mast cells in tissue and on basophils circulating in blood to trigger degranulation (see L. Lichtenstein, *Sci. Am.*, (269) pp. 116–125 (1993)). Activation of A3 adenosine receptors can produce mast cell degranulation and enhance the effect of allergens. Adenosine and antigens trigger an influx of calcium to induce mast cell granules to release their contents an promote synthesis and release of cytokines, prostaglandins and leukotrienes. The various chemicals released by mast cells are responsible for many allergic symptoms. Long term release of these chemicals can induce basophils, eosinophils, and other cells flowing through blood vessels to migrate into the tissue. Migration is promoted due to the expression and activation of adhesion molecules on the circulating cells and on vascular endotheilial cells. The circulating cells adhere to the endothelial cells, roll among them, and eventually cross into the surrounding matrix. These recruited cells secrete chemicals of their own that damage tissue. Thus, there are long term secondary effects which may also be prevented by specific blockade of mast cell degranulation.

The A3 adenosine receptor antagonists are useful for treating patients prone to reperfusion injury, including those with coronary artery diseases in general, and patients anticipating the opening of occluded arteries (reperfusion) by various interventions, e.g. coronary artery bypass grafts, angioplasty or thrombolytic therapy. Heller, L. J. and Regal, J. F., "Effect of adenosine on histamine release and atrioventricular conduction during guinea pig cardia anaphylaxis" *Circ. Res.*, (62) pp. 1147–1158 (1988), suggest that mast cell degranulation is involved in ischemia/reperfusion injury. Adenosine-induced mast cell degranulation during a period of transient ischemia may be responsible for the phenomenon of preconditioning (i.e., a transient ischemic episode reduces myocardial damage resulting from a subsequent prolonged ischemic episode). Accordingly, mast cells are temporarily depleted of damaging mediators during the preconditioning period. Heller et al. found increases in levels of endogenous adenosine during cardiac anaphylaxis contributed to the development of atrioventricular conduction delays and that increases in levels of adenosine before antigen challenge may increase the amount of histamine released during cardiac anaphylactic reactions. Wolff, et al., "Ventricular arrhythmias parallel cardiac histamine efflex after coronary artery occlusion in the dog" *Agents and Actions*, (25) pp. 296–306 (1988), concluded that during acute myocardial ischemia, the coronary sinus histamine concentration increases simultaneously with the development of early ischemic ventricular arrhythmias and in proportion of their severity. Keller, et al., "Acute reoxygenation injury in the isolated rat heart: role of resident cardiac mast cells" *Circ. Res.*, (63) pp. 1044–1052 (1988), found that isolated crystalloid-perfused rat heart is not a leukocyte-free preparation and mast cells resident to the heart play an important role in acute reoxygenation injury. Jolly, et al., "Effects of lodoxamide on ischemic reperfused myocardium" *J. Cardiovas. Pharmacol.*, (4) pp. 441–448 (1982), found that lodoxamide, a drug that acts to inhibit mast cell degranulation, reduces myocardial ischemic injury. Ito et al., "Role of cardiac mast cells in complement C5a-induced myocardial ischemia" *Am. J. Physiol.*, (33) pp. H1346–H1354 (1992), found that cardiac mast cells are involved in complement-induced release of vasoactive eicosanoids, including TxA2.

For example, the A3 receptor antagonists can be used in adjunct therapy with recanulation such as angioplasty and thrombolytic agents for the treatment of reperfusion injury. A probable course of treatment would be acute i.v. formulation followed by at least two weeks oral treatment for those patients undergoing angioplasty or thrombolytic therapy with, for example, TPA or steptokinase. For those patients presenting with angina, chronic oral therapy would be appropriate.

Radioligand Binding Assay

The human A1, A2a, A2b and A3 receptor subtype cDNAs were subcloned into the expression vectors pSVL (Pharmacia, Columbus, Ohio), CMV5 (Mumby, et al., PNAS, (87) pp. 728–732 (1990)) pCDNA1 or pREP (Invitrogen). Transient expression in COS7 cells (monkey kidney cell line, ATCC CRL 1651, ATCC, Rockville, Md.) (Doyl et al. WO 95/11681) was accomplished by transfection of the cloned adenosine receptor cDNAs under the control of the SV40 promoter into mammalian cells, such as COS7. Membranes prepared from the transfected cells were utilized for the determination of binding affinity, selectivity and specificity of the human adenosine receptors for various ligands. Stable expression of the human adenosine receptors in mammalian cells (e.g., CHO, HEK 293) was achieved after integration of the transfected cDNA into the chromosomes of the host cells. These stable cell lines constituently express the cloned human adenosine receptors and can be propagated infinitely. Stable cell lines expressing the human adenosine subtype cDNAs individually can be used in the binding assay to measure the affinity and selectivity of the receptors for adenosine agonists, antagonists and enhancers.

Membranes prepared from transfected COS7 cells were utilized in a binding assay to measure the affinity of agonists and antagonists on the human adenosine receptors. Monolayer cell culture of transfected COS7 cells were dissociated with 1 mM EDTA in phosphate buffered saline and resuspended in 5 mM Tris, pH 7.6/10 mM $MgCl_2$. The cells were subjected to freeze-thaw lysis and the suspension was homogenized in a glass dounce homogenizer. The membranes were pelleted, resuspended in binding buffer, 50 mM Tris pH 7.6/10 mM $MgCl_2$ and incubated with adenosine deaminase before the binding assay. The binding assay was performed by incubating 50–100 μg of membranes with increasing concentrations of radiolabeled adenosine agonists. Bound ligand was separated from free ligand by filtration on a Skatron cell harvester equipped with a receptor binding filtermat. Bound radioactivity was measured by scintillation counting. Binding data were analyzed by the use on nonlinear regression curve fitting program Graph Pad InPlot, Version 3.0 (Graph Pad Software, San Diego). $K_i$ values were calculated using the Cheng-Prusoff derivation (Cheng, Y. C. and Prusoff, H. R. (1973) Biochem. Pharmacol. 22, 3099–3108). The affinities of agonists and antagonists on human adenosine receptor subtypes were measured in competition binding assays using the radiolabeled adenosine agonists, [$^3$H]-cyclo-hexyladenosine (CHA) for A1 receptors, [$^3$H]-CGS21680 (2-(p-(2-carboxyethyl)-phenylamino)-5'-N-ethyl-carboxamidoadenosine) for A2a receptors and, [$^3$H]-5'-N-ethylcarboxamido adenosine ([$^3$H]-NECA), or [$^{125}$I]-$N^6$-aminobenzyl adenosine ($^{125}$I-ABA) for A3 receptors. Nonselective binding was determined with 1 μM I-ABA for $A_1$ and $A_3$ receptors and 10 μM NECA for $A_{2a}$ receptors. Activity on $A_{2b}$ receptor subtypes was measured in the cAMP accumulation assay described below.

cAMP Accumulation Assay

The changes in cAMP accumulation were measured in stably transfected CHO cells expressing the human adenosine receptor subtypes. CHO cells were washed twice in phosphate buffered saline (PBS) and detached in 0.2% EDTA in PBS. After pelleting at 800 rpm for 10 min, cells were resuspended in KRH buffer (140 mM NaCl/5 mM KCl/2 mM $CaCl_2$/1.2 mM $MgSO_4$/1.2 mM $KH_2PO_4$/6 mM glucose/25 mM Hepes buffer, pH 7.4), washed once in KRH buffer and resuspended at $10^7$ cells/mL. The cell suspension (100 μL) was mixed with 100 μL of KRH buffer containing 200 μM of the phosphodiesterase inhibitor Ro 20-1724 and incubated at 37° C. for 15 minutes. Antagonists were pre-incubated for 10 minutes before adding 5 μM forskolin and 60 μM adenosine. After 10 minutes, 400 μL of 100 mM acetic acid was added and the sample was boiled for 5 minutes. The supernatant was recovered by centrifugation for 15 minutes and cAMP levels were determined by radioimmunoassay (RIANEN kit, DuPont/NEN) using the acetylation protocol. For measurement on $A_{2b}$ receptors, the increase in cAMP accumulation was induced by addition of adenosine (10 μM) and incubated at 37° C. for 20 minutes before termination with acidic acid and RIA analysis.

In determining the quantities of antagonist necessary to block adenosine binding to the A3 receptor, persons skilled in the art would recognize that an A3 adenosine receptor antagonist with high affinity for the receptor can be administered at dosages lower than A3 adenosine receptor antagonists with low affinity. A3 adenosine receptor antagonists having a pKi of greater than about 7 for the A3 receptor and below about 6 for other adenosine receptor subtypes, may be administered by any effective means to achieve either localized or systemic contact of the A3 adenosine receptor antagonist with target A3 adenosine receptors, including intravenous, intramuscular, intrasynovial, intranasal, nebulized intrapulmanory, intraperitoneal or other common means for administration of therapeutic compounds. Dosages of between about 1 μg/kg and 10 mg/kg are envisioned, as necessary, to achieve the desired effect of A3 adenosine receptor blockade.

FIG. 1 shows antagonist activity of compound IV on human A3 adenosine receptors stably expressed on CHO cells. Inclusion of compound IV prevents the inhibition of cAMP accumulation resulting from adenosine activation of $A_3$ receptors. Compound IV had no effect on basal cAMP levels or levels of cAMP accumulated with forskolin alone.

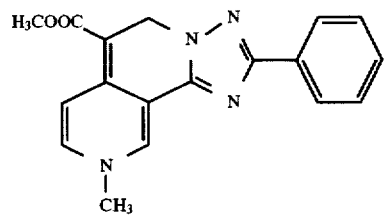

in the cAMP accumulation assay.

The following examples are provided to further define but not to limit the invention defined by the foregoing description and the claims which follow:

Selectivity for the A3 Adenosine Receptor $IC_{50}$ values, representing the amount of

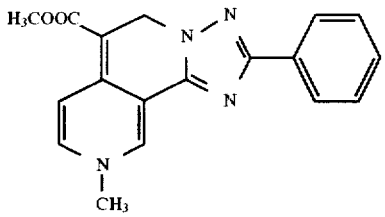

required to inhibit specific binding of the radioligand to the A1, A2a, or A3 receptors by 50%, and cAMP accumulation via A2b receptors were determined.

| Receptor | $IC_{50}$ |
| --- | --- |
| A1 | 5.3 µM |
| A2a | 27.5 µM |
| A2b | – (inactive at 10 µM) |
| A3 | 13 nM |

The binding data shows the compounds described above have nM affinity for the A3 receptor and are highly selective for the A3 receptor. Such A3 selectivity minimizes oor eliminates side effects associated with other adenosine receptor subtypes such as cardiovascular effects, e.g. hypotension, bradycardia, arrthymias, and CNS effects, e.g. sedation, locomotion.

Specific Inhibition of Adenosine Induced Vascular Constriction

The vasoconstrictor action of adenosine in hamster cheek pouch arterioles is described here, and blockade of this response by A3 adenosine receptor antagonists is demonstrated. Adenosine, inosine, cromolyn, compound 48/80, methylene blue, acetylcholine, and components for saline solutions used to bathe arterioles are obtained from Sigma. 8(p-sulphophenyl)theo-phylline was obtained from Research Biochemicals, Inc. (Natick, Mass.).

Arterioles (luminal diameter approximately 60 µm) are dissected from male Golden hamster cheek pouches, transferred to a 37° C. tissue chamber, and cannulated at both ends (see Duling et al., Am. J. Physiol., (241) (Heart Circ. Physiol., (10) pp. H108–H116 (1981); Duling et al., Microcirculatory Technology, edited by C. H. Baker and W. G. Nastuk, Orlando Academic Press, pp. 265–280 (1986)). Changes in luminal diameter in response to abluminal delivery of adenosine ($10^{-8}$ M to $10^{-4}$ M) are measured using videotaped microscopic observation and video calipers with continuous output, to generate cumulative concentration-response curves. These curves are discovered to be biphasic: $10^{-6}$ M adenosine elicited an intense, transient constriction and higher concentrations induced dilator responses. Pretreatment (100 µM) with 8(p-sulfophenyl) theophylline, SPT, a nonspecific adenosine receptor antagonist, inhibited the dilator responses but did not alter the constriction. Without more, this result is consistent with the interpretation that the constrictor response is not mediated through an adenosine A1 or A2 receptor.

The constrictor response is assymetrical and focal in nature, such that it was initiated at discrete points and subsequently spread along the entire vessel, suggesting discrete sites of action of adenosine. Examination of the abluminal surface of the vessel after staining with methylene blue reveal large numbers of mast cells closely associated with the vessel wall. Following exposure to adenosine, mast cells are found to be degranulated, suggesting the involvement of mast cell granule contents in the constrictor response. This finding is consistent with reports that adenosine potentiates the release of granule contents from mast cells isolated from rat peritoneum, and that mast cell degranulation causes constriction in some vascular beds resulting in C5a-induced myocardial ischemia, mast cell-dependent inflammation, brain arteriole diameter constriction, and the release of allergic mediators.

Following the above procedure, an antagonist of the formula described above is used to treat tissue, and found to inhibit constriction.

Reduction of Myocardial Infarct Size in Anesthetized Dogs

The effect of antagonist compound IV, with high affinity for canine $A_3$ adenosine receptors, on myocardial infarct size is compared to a vehicle-treated control group in barbital-anesthetized dogs subjected to 90 minutes of left anterior descending coronary artery occlusion followed by 3 hours of reperfilsion. Vehicle (5 µM NaOH in isotonic saline) or antagonist are infused at a rate of 1 ml/min directly into the left anterior descending coronary artery distal to the occlusion site beginning 10 minutes before occlusion and are continued throughout the entire ischemic period. The myocardial region at risk and infarct size are determined by the triphenyltetrazolium histochemical technique and regional myocardial blood flow by radioactive microspheres. Coronary sinus LDH activity and histamine concentrations were measured at various times throughout the experiments and myeloperoxidase activity was determined at the conclusion of the experiments as an index of neutrophil infiltration into the ischemic-reperfused mycocardium. Ten dogs were included in this preliminary study, 4 in the vehicle-treated group and 6 in the antagonist treated group.

In all animals, arrhythmias are encountered during occlusion and reperfusion and some dogs from each group progress to ventricular fibrillation requiring cardioversion. Hemodynamics and regional myocardial blood flow in the non-ischemic left circumflex coronary artery region are not different between groups at baseline or during occlusion although during reperfusion dP/dt is significantly improved and left anterior descending coronary artery blood flow was significantly decreased in antagonist treated dogs. In the ischemic-reperfused region, collateral blood flow during the occlusion period (the major determinant of ultimate infarct size) was slightly greater in antagonist-treated dogs, particularly in the subepicardial region. In addition, coronary sinus LDH activity and histamine concentrations are reduced in the antagonist-treated group during reperfusion. Finally, myeloperoxidase activity activity is not different between the two groups although there is a tendency for reduced activity in drug-treated animals in infarcted tissue. Compound IV effectively reduces myocardial infarct size in anesthetized dogs by a direct cardioprotective action.

While the foregoing specification teaches the principles of the present invention, with examples provided for the purpose of illustration, it will be understood that the practice of the invention encompasses all of the usual variations, adaptations, modifications, as come within the scope of the following claims and its equivalents.

EXAMPLE 1

Asthma Treatment

The A3 adenosine receptor antagonists can also be administered by inhalation. Commercially available nebulizers for liquid formulations, including jet nebulizers and ultrasonic nebulizers are useful for such administration. Liquid formulations can be directly nebulized and lyophilized powder can be nebulized after reconstitution.

For administration by inhalation, the antagonists are conveniently delivered in the form of an aerosol spray presentation from pressurized packs or nebulizers. The compounds may also be delivered as powders which may be formulated and the powder composition may be inhaled with the aid of an insufflation powder inhaler device.

An exemplary delivery system for inhalation is a metered dose inhalation (MDI) aerosol, which may be formulated as a suspension or solution of an A3 adenosine receptor antagonist in suitable propellants, such as fluorocarbons or hydrocarbons.

| Aerosol | Per canister |
|---|---|
| compound IV | 24 mg |
| Lecithin, NF Liquid Concentrate | 1.2 mg |
| Trichlorofluoromethane, NF | 4.025 g |
| Dichlorodifluoromethane, NF | 12.15 g |

The aerosol formulation is prepared according to conventional procedures and administered to a patient experiencing an asthmatic episode.

EXAMPLE 2

Treatment of Allergies Caused by Airborne Allergens

Tablets and capsules represent a dosage form suitable for patients suffering from allergies caused by airborne allergens. To make a tablet, the antagonist, in a free-flowing form such as powder or granules, is introduced to a suitable machine, optionally mixed with a binder, lubricant, inert diluent, surface active or dispersing agent. Desirably, each tablet contains from about 2.5 mg to about 500 mg of the antagonist and each cachet or capsule contains from about 2.5 to about 500 mg of the antagonist.

The following are representative tablet and capsule formulations:

| Tablet | mg/tablet |
|---|---|
| compound IV | 25 |
| Microcrystalline Cellulose | 415 |
| Pregelatinized Starch | 43.5 |
| Magnesium Stearate | 2.5 |
| Capsule | mg/capsule |
| compound IV | 25 |
| Lactose Powder | 573.5 |
| Magnesium Stearate | 1.5 |

A patient suffering from allergies caused by airborne allergens takes 1 or 4 tablets or capsules each day to alleviate and/or prevent allergy symptoms

EXAMPLE 3

Psoriasis Treatment

Included within the invention are preparations for topical application to the skin whereby the A3 adenosine receptor antagonists are effective in the treatment and control of skin diseases characterized by rapid rates of cell proliferation and/or abnormal cell proliferation, e.g., psoriasis.

In a preferred method of treating hyperproliferative skin diseases, a pharmaceutical formulation comprising an A3 adenosine receptor antagonist (usually in concentrations in the range of from about 0.001 percent to about 10 percent, preferably from about 0.1 percent to about 5 percent), together with a non-toxic, pharmaceutically acceptable topical carrier, is applied several times daily to the affected skin until the condition is improved. Topical applications may then be continued at less frequent intervals (e.g., once a day) to control mitosis in order to prevent return of severe disease conditions.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

| Ointment | mg/g |
|---|---|
| compound IV | 1.0–20.0 |
| Benzyl Alcohol, NF | 20.0 |
| Mineral Oil, USP | 50.0 |
| White Petrolatum, USP to make | 1.0 g |

A patient suffering from psoriasis administers the ointment to affected areas several times each day.

EXAMPLE 4

Recanulation Treatment

Compound IV is used in adjunct therapy with recanulation such as angioplasty and thrombolytic agents for the treatment of reperfusion injury.

An i.v. formulation such as

| | |
|---|---|
| compound IV | 0.5–10.0 mg |
| Sodium Citrate | 5–50 mg |
| Citric Acid | 1–15 mg |
| Sodium Chloride | 1–8 mg |
| Water for Injection (USP) | q.s. to 1 L | is administered to a patient undergoing angioplasty or thrombolytic therapy. For preparation of the formulation, compound IV is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994)

Following i.v. teatment, oral compositions of the compound, such as

| Tablet | mg/tablet |
|---|---|
| compound IV | 25 |
| Microcrystalline Cellulose | 415 |
| Pregelatinized Starch | 43.5 |
| Magnesium Stearate | 2.5 | are administered for two weeks.

What is claimed is:

1. A method for treating or preventing asthma in a patient comprising administering to the patient a compound of the formula

19

[Structure I shown]

and pharmaceutically acceptable salts, wherein $R^1$ is
  (a) phenyl or pyrimidyl optionally substituted with one or two substituents selected from the group consisting essentially of $C_1$–$C_4$-alkyl, bromo, chloro, fluoro, $CF_3$, $C_1$–$C_4$-alkoxy and phenyl, or
  (b) furyl, thiophenyl or thiazolyl optionally susbtituted with $C_1$–$C_4$-alkyl or phenyl;

$R^2$ is
  hydrogen, $C_1$–$C_4$-alkyl or phenyl;

$R^3$ is
  —CN, —COOC$_{1-4}$ alkyl, —CONH$_2$, —COOH, —CONHSO$_2$R$^5$ or 5-tetrazolyl;

$R^4$ is
  —C$_{1-4}$-alkyl optionally substituted with —COOC$_{1-4}$ alkyl, —CONH$_2$, COOH or phenyl optionally substituted with one or two substituents selected from the group consisting essentially of $C_1$–$C_4$-alkyl, bromo, chloro, fluoro, $CF_3$, $C_1$–$C_4$-alkoxy and phenyl; and $R^5$ is
  —$C_1$–$C_4$-alkyl or phenyl optionally substituted with one or two substituents selected from the group consisting essentially of $C_1$–$C_4$-alkyl, bromo, chloro, fluoro, $CF_3$, $C_1$–$C_4$-alkoxy and phenyl.

2. A method of claim 1, wherein the compound has the formula

[Structure II shown]

and pharmaceutically acceptable salts, wherein $R^1$ is
  phenyl optionally substituted with one or two substituents selected from the group consisting of $C_1$–$C_4$-alkyl, bromo, chloro, fluoro, $CF_3$, $C_1$–$C_4$-alkoxy and phenyl, or $R^2$ is
  hydrogen, $C_1$–$C_4$-alkyl or phenyl;

$R^3$ is
  —CN, —COOC$_{1-4}$ alkyl, —CONH$_2$, —COOH, —CONHSO$_2$R$^5$ or 5-tetrazolyl;

20

$R^4$ is
  $C_{1-4}$-alkyl optionally substituted with —COOC$_{1-4}$ alkyl, —CONH$_2$, COOH or phenyl, optionally substituted with one or two substituents selected from the group consisting of $C_1$–$C_4$-alkyl, bromo, chloro, fluoro, $CF_3$, $C_1$–$C_4$-alkoxy and phenyl; and $R^5$ is
  $C_1$–$C_4$-alkyl or phenyl optionally substituted with one or two substituents selected from the group consisting of $C_1$–$C_4$-alkyl, bromo, chloro, fluoro, $CF_3$, $C_1$–$C_4$-alkoxy and phenyl.

3. A method of claim 2, wherein the compound has the formula

[Structure III shown]

and pharmaceutically acceptable salts, wherein $R^1$ is
  phenyl optionally substituted with one or two substituents selected from the group consisting of $C_1$–$C_4$-alkyl, bromo, chloro, fluoro, $CF_3$, $C_1$–$C_4$-alkoxy and phenyl, or $R^2$ is
  hydrogen, $C_1$–$C_4$-alkyl or phenyl;

$R^3$ is
  —COOCH$_3$ or —COOCH$_2$CH$_3$;

$R^4$ is
  —CH$_3$, —CH$_2$CH$_3$, —CH$_2$COOCH$_3$, —CH$_2$COOC(CH$_3$)$_3$, —CH$_2$COOH, -benzyl, 4-bromobenzyl or 4-chlorobenzyl; and $R^5$ is
  $C_1$–$C_4$-alkyl or phenyl optionally substituted with one or two substituents selected from the group consisting of $C_1$–$C_4$-alkyl, bromo, chloro, fluoro, $CF_3$, $C_1$–$C_4$-alkoxy and phenyl.

4. A method of claim 3, wherein the compound has the formula

[Structure IV shown]

and pharmaceutically acceptable salts.

5. A method of claim 4, wherein the salt is the pharmaceutically acceptable salt is the methanesulfonic acid salt.

* * * * *